United States Patent
Schultz

(10) Patent No.: US 8,430,864 B2
(45) Date of Patent: Apr. 30, 2013

(54) CATHETER WITH MULTIPLE DEFLECTIONS

(75) Inventor: Jeffrey W. Schultz, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 13/029,056

(22) Filed: Feb. 16, 2011

(65) Prior Publication Data

US 2012/0209143 A1   Aug. 16, 2012

(51) Int. Cl.
*A61M 25/00* (2006.01)
*A61M 25/098* (2006.01)

(52) U.S. Cl.
USPC ........... 604/528; 600/585; 604/523; 604/529; 604/532

(58) Field of Classification Search ............... 600/585; 604/523–539
See application file for complete search history.

(56) References Cited

U.S. PATENT DOCUMENTS

| | | | |
|---|---|---|---|
| 3,500,820 A | | 3/1970 | Almen |
| 5,325,845 A | * | 7/1994 | Adair .............................. 600/114 |
| 5,334,145 A | * | 8/1994 | Lundquist et al. .......... 604/95.04 |
| 5,391,199 A | | 2/1995 | Ben-Haim |
| 5,441,483 A | * | 8/1995 | Avitall ........................ 604/95.05 |
| 5,487,757 A | * | 1/1996 | Truckai et al. .................. 604/264 |
| 5,882,333 A | | 3/1999 | Schaer et al. |
| 6,066,125 A | * | 5/2000 | Webster, Jr. .................... 604/528 |
| 6,198,974 B1 | | 3/2001 | Webster, Jr. |
| 6,201,387 B1 | | 3/2001 | Govari |
| 6,485,455 B1 | | 11/2002 | Thompson et al. |
| 6,610,058 B2 | | 8/2003 | Flores |
| 6,926,669 B1 | * | 8/2005 | Stewart et al. ................. 600/439 |
| 7,008,401 B2 | | 3/2006 | Thompson et al. |
| 7,187,963 B2 | | 3/2007 | Coleman et al. |
| 7,402,141 B2 | | 7/2008 | Heuser |
| 7,465,288 B2 | * | 12/2008 | Dudney et al. .............. 604/95.04 |
| 2006/0149129 A1 | | 7/2006 | Watts et al. |
| 2010/0004591 A1 | | 1/2010 | Barenboym et al. |
| 2010/0022948 A1 | | 1/2010 | Wilson et al. |

FOREIGN PATENT DOCUMENTS

| | | |
|---|---|---|
| EP | 1 323 448 A2 | 7/2003 |
| EP | 1 532 999 A2 | 5/2005 |

OTHER PUBLICATIONS

Extended European Search Report dated May 7, 2012 for corresponding European Application No. 12155638.5 (10 pages).

* cited by examiner

*Primary Examiner* — Rene Towa
*Assistant Examiner* — Adam Eiseman
(74) *Attorney, Agent, or Firm* — Christie, Parker & Hale, LLP

(57) ABSTRACT

A catheter has a control handle with at least an outer thumb control and an inner second thumb control. A longer puller wire has a distal end anchored at or near a distal end of distal deflectable portion. A shorter puller wire has a distal end anchored at or near a distal end of the proximal deflectable portion. For the shorter puller wire, a shorter compression coil has a distal end at or near a proximal end of the intermediate deflectable section. For the longer puller wire, a longer compression coil has a distal end at or near a distal end of the shorter puller wire. The inner and outer thumb controls include engagement members releasable by rotation of one thumb control relative to the other. When disengaged, the thumb controls each can be moved longitudinally relative to each other. When engaged, the thumb controls are coupled together for longitudinal movement as a single unit relative to the control handle.

20 Claims, 7 Drawing Sheets

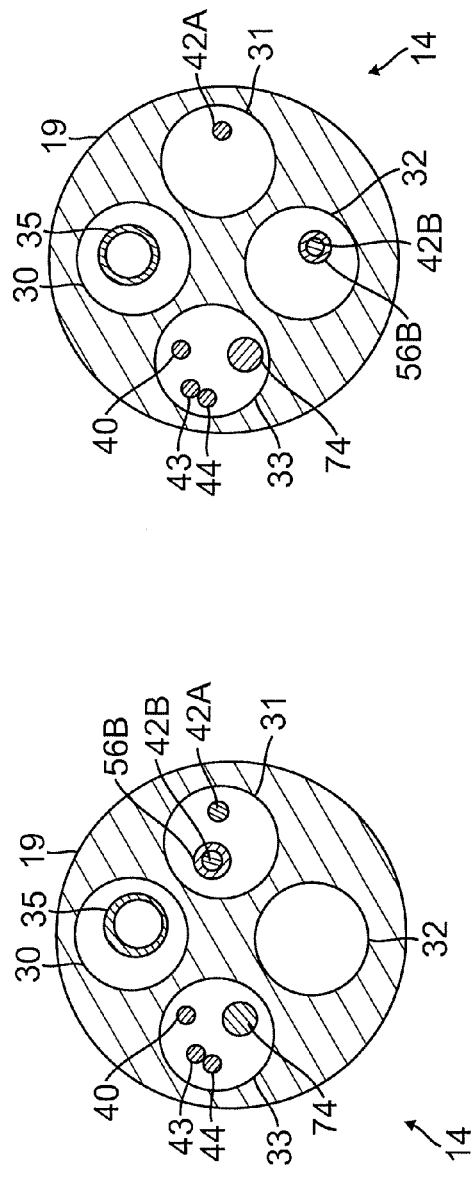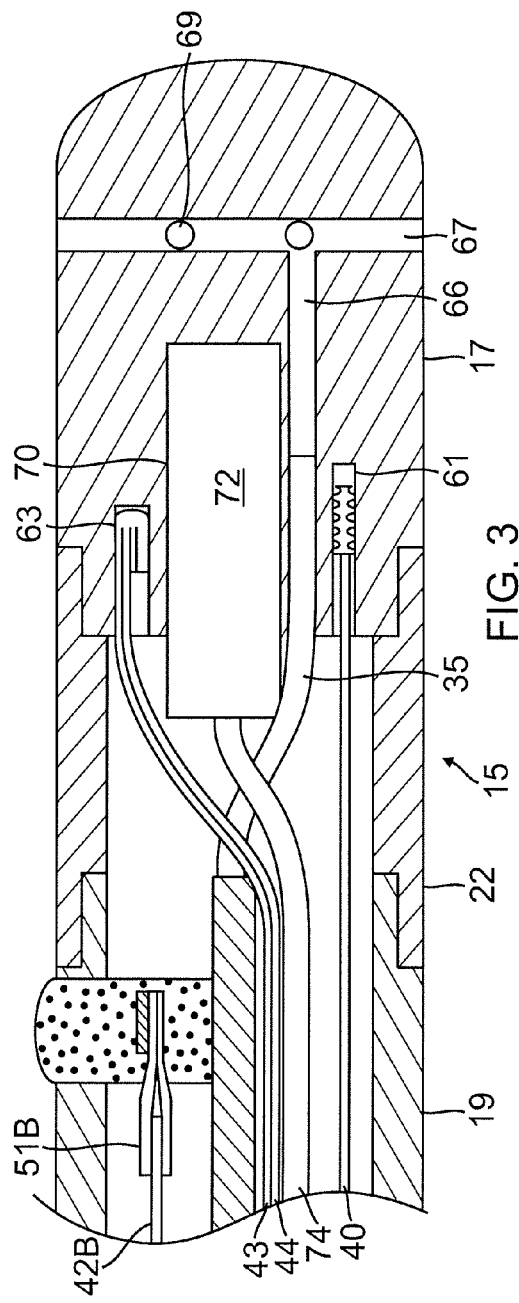

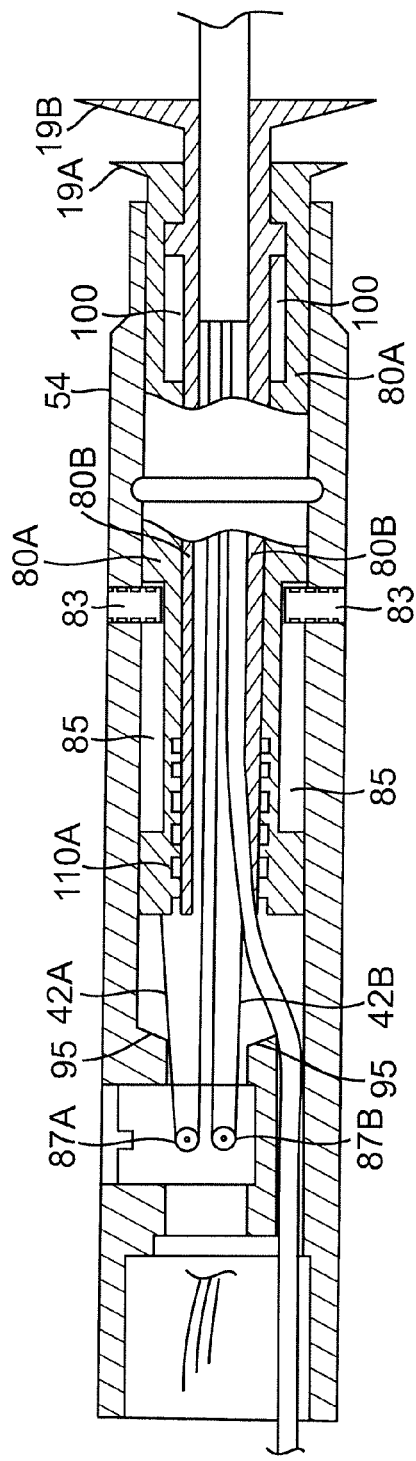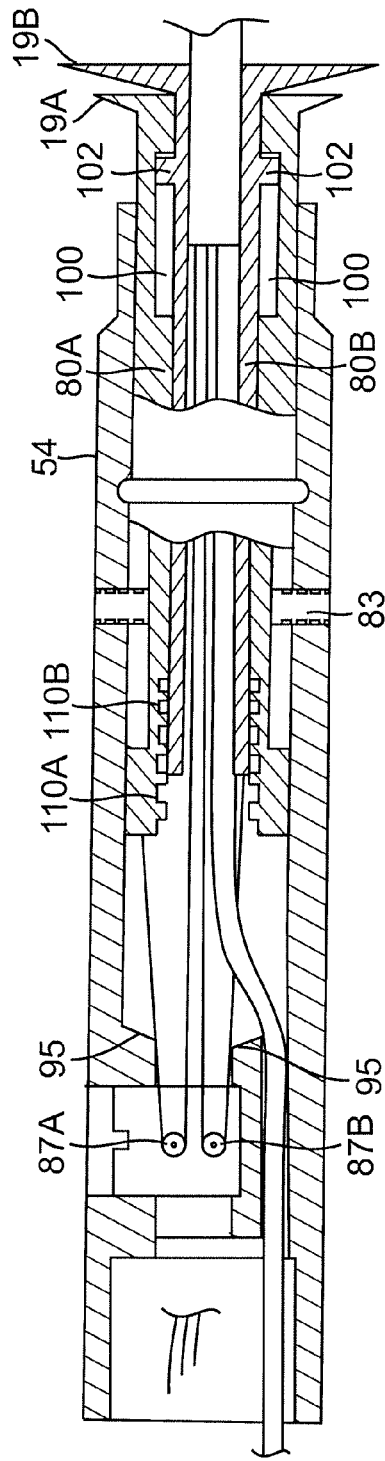

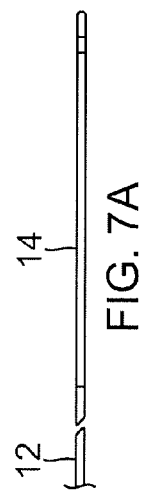
FIG. 7A
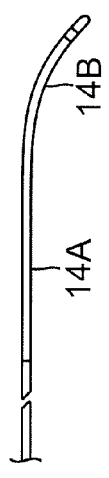
FIG. 7B
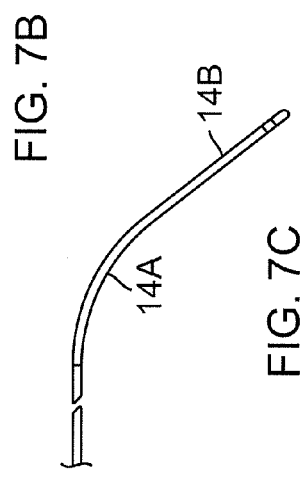
FIG. 7C
FIG. 7D
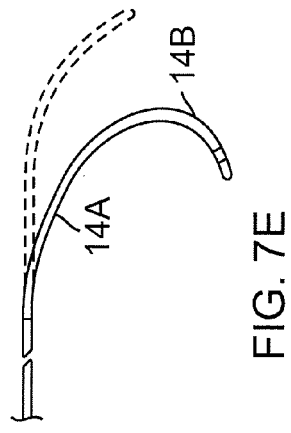
FIG. 7E
FIG. 7F
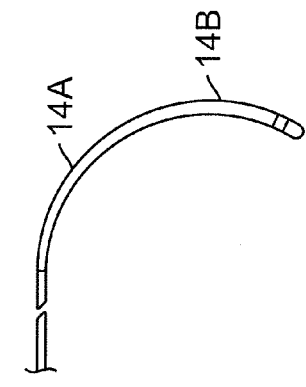
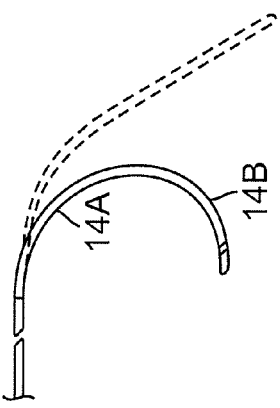

CATHETER WITH MULTIPLE DEFLECTIONS

FIELD OF INVENTION

This invention relates to a catheter, in particular, a catheter adapted to provide compound curves of deflectable regions.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters adapted to measure activity within the heart.

In use, the electrode catheter is inserted into a major vein or artery, e.g., femoral artery, and guided into a chamber of the heart. Within the chamber, the catheter is maneuvered through movements that include deflection of a distal portion of the catheter so that the tip electrode is positioned at a target location on the heart wall in the heart chamber for mapping and/or ablation. The ability to control the exact position and orientation of the catheter is critical and largely determines how useful the catheter is.

Accordingly, a desire exists for a catheter that can provide more variations in deflection curvature, especially in different sections along the catheter. A desire also exists for a catheter that can provide a pre-deflection such that manipulation of the control handle increases the curvature of the pre-deflection along with the remainder of the catheter. Such a catheter should provide a control handle by which multiple deflections can be controlled by a single movement.

SUMMARY OF THE INVENTION

The present invention is directed to a catheter having two or more puller wires whose distal ends are anchored at different locations of a deflectable section to achieve nonuniform curve profiles. This structure allows for compound curves of different portions of the deflectable sections of catheters such as those used in electrophysiology (EP) for the diagnosis and treatment of arrhythmias. In the case of an EP catheter with a catheter body, a deflectable section and two puller wires of different lengths, distal ends of the puller wires are anchored at different locations of the deflectable section, with a compression coil surrounding the shorter puller wire with the compression coil terminating at a transition between the catheter body and the deflectable section, and a compression coil surrounding the longer puller wire with the compression coil terminating at a distal end of the shorter puller wire. By manipulating the shorter puller wire via the control handle, a proximal section of the deflectable section through which the shorter puller wire extends is deflected. By manipulating the longer puller wire via the control handle, a distal section of the deflectable section through which the longer puller wire extends is deflected. By manipulating both the longer and the shorter puller wires, deflection of the deflectable section in its entirety is accomplished. By varying the distal anchor locations of the puller wires, the degree of curvature or deflection can be varied, such that the deflection curvatures of the proximal and distal sections of the deflection can have the same radius or one section can have a tighter radius than the other.

Control of a plurality of puller wires is achieved via a control handle with a common plurality of nested thumb controls. The puller wires extend into the control handle and each is wrapped around a respective pulley mounted in the control handle, with the proximal end of each puller wire being anchored in a respective thumb control, such that a user actuating a thumb control by moving it distally relative to the control handle draws on the respective puller wire anchored thereto. The control handle is configured to allow each thumb control to be manipulated independently allowing for precise control over the corresponding section of the deflectable section through which the respective puller wire extends. Releasable engagement members, such as interlocking teeth, are provided on each thumb control to allow for releasable coupling of the thumb control(s) to adjacent thumb control(s) so that all puller wires can be manipulated by movement of one thumb control. As such, simultaneous deflection of each portion of the deflectable section is accomplished in a single movement of one thumb control. Moreover, pre-deflection of any one or more sections is possible followed by simultaneous deflection of multiple portions as a unit.

In one embodiment, the catheter of the present invention includes an elongated catheter body, a deflectable intermediate section having at least a distal deflectable portion and a proximal deflectable portion, and a control handle proximal the elongated body where the control handle includes at least an outer thumb control and an inner second thumb control. A longer puller wire has a proximal end anchored in the inner thumb control and a distal end anchored at or near a distal end of distal deflectable portion. A shorter puller wire has a proximal end anchored in the outer thumb control and a distal end anchored at or near a distal end of the proximal deflectable portion. Surrounding the shorter puller wire, a shorter compression coil has a distal end at or near a proximal end of the intermediate deflectable section. Surrounding the longer puller wire, a longer compression coil has a distal end at or near a distal end of the shorter puller wire. The inner and outer thumb controls include releasable engagement members that allow the thumb controls to be movable between disengaged and engaged positions by rotation of one thumb control relative to the other. When disengaged, the thumb controls each can be moved longitudinally relative to each other. When engaged, the thumb controls are coupled together for longitudinal movement as a single unit relative to the control handle.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2A is a longitudinal cross sectional view of the intermediate section of FIG. 2, taken along line A-A.

FIG. 2B is a longitudinal cross sectional view of an alternate embodiment of the intermediate section.

FIG. 3 is a side cross-sectional view of an embodiment of a distal section, taken along a diameter.

FIG. 5 is a side cross-sectional view of an embodiment of a control handle with thumb controls in a disengaged configuration.

FIG. 6 is a side cross-sectional view of an embodiment of a control handle with thumb controls in another engaged configuration.

FIGS. 7A-F illustrate various deflections resulting from selective engagement and manipulation of the thumb controls.

DETAILED DESCRIPTION OF THE INVENTION

Figure 1:
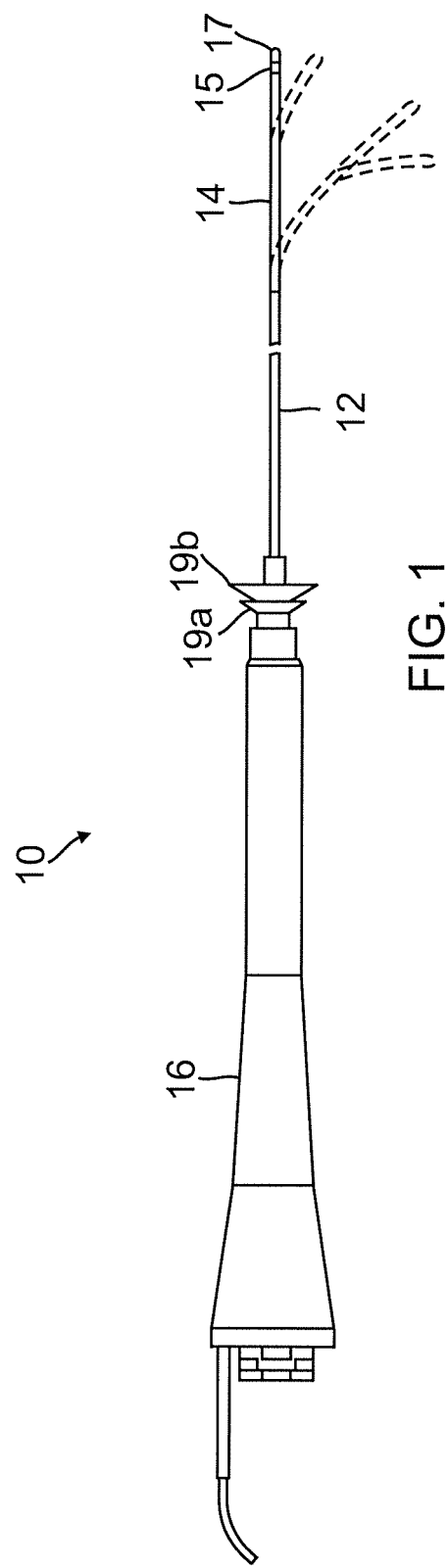
FIG. 1 is a top plan view of one embodiment of the catheter of the present invention.

Referring to FIG. 1, the present invention is directed to a catheter 10 with a catheter body 12, an intermediate deflectable section 14 and a distal end section 15, including a tip electrode 17. At the proximal end of the catheter body 12 is a control handle 16 with a plurality of thumb controls, for example, 19a and 19b, manipulated by a user to accomplish a variety of independent and combined deflections of the intermediate section 14. In accordance with a feature of the invention, the thumb controls can be disengaged for independent manipulation to provide independent deflection of a selected portion of the intermediate section, or releasably engaged in different configurations for joint manipulation to provide different selected combined deflections of the intermediate section.

Figure 2:
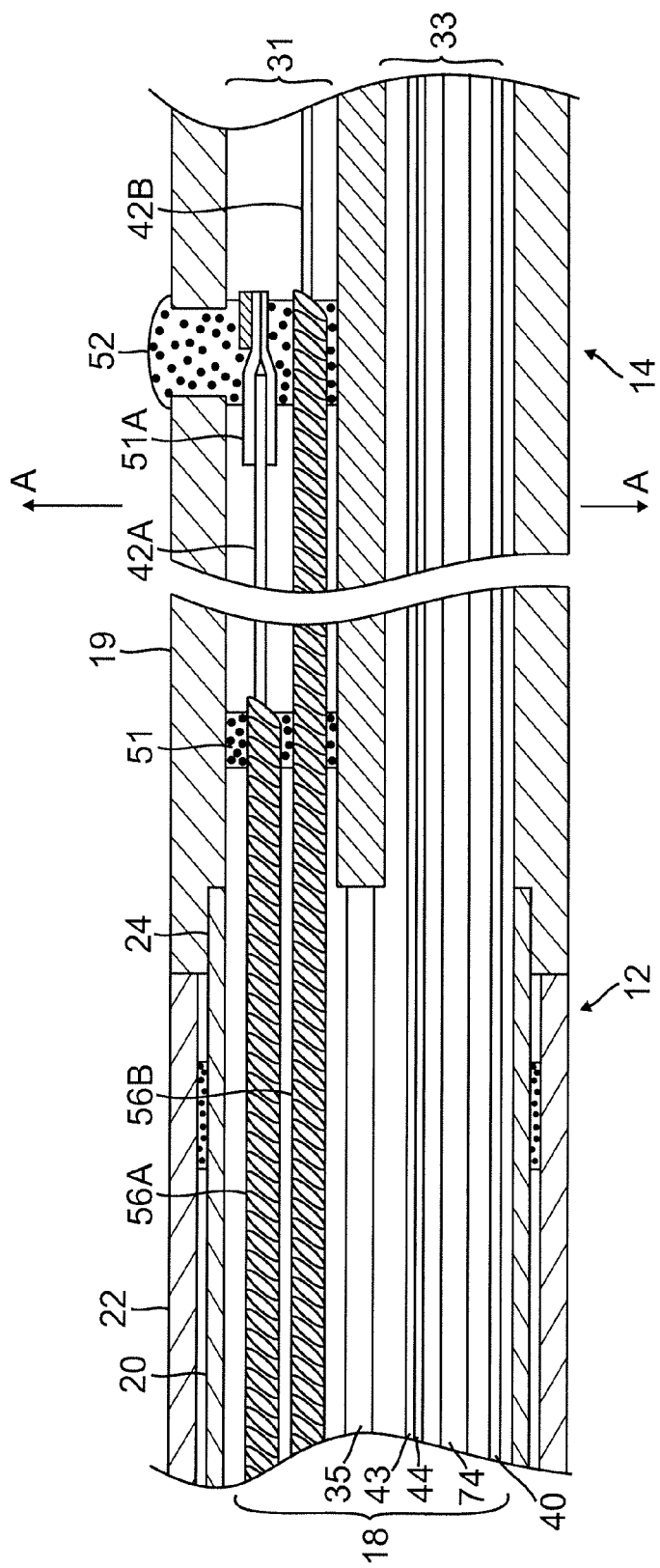
FIG. 2 is a side cross-sectional view of an embodiment of a junction of a catheter body and an intermediate section, taken along a diameter.

With reference to FIG. 2, the catheter body 12 comprises a single, central or axial lumen 18. The catheter body 12 is flexible, i.e., bendable, but substantially non-compressible along its length. The catheter body 12 may be of any suitable construction and made of any suitable material. A suitable construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner. A single lumen catheter body 12 can be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, e.g., polyimide. The stiffening tube 20 is held in place relative to the outer wall 22 at the proximal end of the catheter body 12. A first glue joint (not shown) is made between the distal ends of the stiffening tube 20 and the outer wall 22 by a fast drying glue, e.g. Super Glue®. Thereafter a second glue joint 26 is formed between the proximal ends of the stiffening tube 20 and outer wall 22 using a slower drying but stronger glue, e.g., polyurethane.

The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

As shown in FIGS. 2 and 2A, the intermediate section 14 comprises a shorter section of tubing 19 with multiple off-axis lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIG. 2. The proximal end of the intermediate section 14 comprises an inner counter bore 24 that receives the outer surface of the polyimide stiffener 20. The intermediate section 14 and catheter body 12 are attached by glue 29 or the like.

As illustrated in FIG. 3, the tip section 15 includes the tip electrode 17 which may be connected to the tubing 19 of the intermediate section 14 by means of a single lumen connector tubing 22. The connector tubing provides transition space for the various components extending from the tubing 22 to reorient themselves as needed for anchoring in the tip electrode 17. To that end, a distal surface of the tip electrode is provided with blind holes. In the disclosed embodiment, blind hole 61 is provided to receive a distal end of the tip electrode lead wire 40, blind hole 63 to receive a distal end of the thermocouple wires 43 and 44. Irrigation passage 66 is also formed in the tip electrode to receive a distal end of the irrigation tubing 35. The passage 66 is in communication with transverse branches 67 and fluid ports 69 allowing fluid delivered through the tubing 35 to pass to outside of the tip electrode. A blind hole 70 is also provided to receive a distal end of an electromagnetic position sensor. The electromagnetic sensor 72 is connected to an electromagnetic sensor cable 74, which extends through the fourth lumen 34 of the tip section 14 through the catheter body 12 into the control handle 16. The electromagnetic sensor cable 74 comprises multiple wires encased within a plastic sheath. In the control handle 16, the wires of the sensor-cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. Suitable electromagnetic sensors for use in connection with the present invention are described, for example, in U.S. Pat. Nos. 5,391,199 and 6,201,387, entitled "Miniaturized Position Sensor," the disclosures of which are incorporated herein by reference. A preferred electromagnetic mapping sensor 72 is manufactured by Biosense Webster, Inc. and marketed under the trade designation NOGA.

As shown in FIGS. 2 and 2A, extending through the single lumen 18 of the catheter body 12 are various components, for example, lead wire 40 for the tip electrode, thermocouple wires 43 and 44, sensor cable 74, irrigation tubing 35 and multiple puller members 42, and any other wires or cables. Passing distally into first lumen 30 of the tubing 19 of the intermediate deflectable section is the irrigation tubing 35. Passing distally into fourth lumen 33 of the tubing are tip electrode lead wire 40, thermocouple wires 43, 44 and sensor cable 74. Passing distally into second lumen 31 are a first and shorter puller member 42A and a second and longer puller member 42B. In particular, longitudinal movement of the puller wire(s), relative to the catheter body 12 enables a user to deflect selected portion(s) of the intermediate section via the thumb controls 19a, 19b of the control handle.

As shown in FIGS. 2 and 3, the distal ends of the deflection puller members 42 are anchored to the outer wall of the tubing 19 of the intermediate deflectable section by means of T-anchors 51. In accordance with a feature of the present invention, a distal anchor location of the distal end of the first and shorter puller member 42A (as represented by the location of T-anchor 51A) is proximal of a distal anchor location of the distal end of the second and longer puller member (as represented by the location of T-anchor 51B). In one embodiment, the anchor location of the shorter puller member is at or near a midpoint of the length of the tubing 19, and the anchor location of the distal end of the longer puller member is near the distal end of the tubing 19. In the intermediate section 14, each puller member 42 extends through a plastic, e.g., Teflon®, sheath (not shown), which prevents the puller members 42 from cutting into the wall of the tubing 19 of the intermediate section 14 when the intermediate section 14 is deflected.

As shown in FIG. 2A, each puller member has a respective compression coil 56 in surrounding relation therewith. The compression coils 56A, 56B are made of any suitable metal, e.g., stainless steel. The compression coils 56 are tightly wound on itself to provide flexibility, i.e., bending, but to resist compression. The inner diameter of the compression coils 56 is preferably slightly larger than the diameter of the puller wires 42. For example, when a puller member 42 has a diameter of about 0.007 inches, the compression coil 56 preferably has an inner diameter of about 0.008 inches. The Teflon® coating on the puller member 42 allows them to slide freely within the compression coils. The outer surface of the compression coils can be covered by a flexible, non-conductive sheath to prevent contact between the compression coils and other components, such as lead wires and cables, etc. The non-conductive sheath can be made of polyimide tubing. In accordance with a feature of the present invention, the compression coil 56A for the shorter puller member 42A extends from the proximal end of the catheter body 12 to the proximal end of the intermediate section 14, and the compression coil 56B for the longer puller member 56B extends from the proximal end of the catheter body 12 to at or near the distal anchor location of the shorter puller member 42A. The compression coils 56 are anchored at their proximal ends to the proximal end of the stiffening tube 20 in the catheter body 12 by a glue joint 50 (not shown) and at their distal ends near their respective distal anchor locations by glue joints 51 and 52 (FIG. 2). In the illustrated embodiment, the puller wires 42A, 42B and their respective compression coils 56A, 56B define in the intermediate section 14 a proximal portion 14A and a distal portion 14B, where the portions 14A, 14B can be independently deflected and simultaneously deflected.

Figure 4:
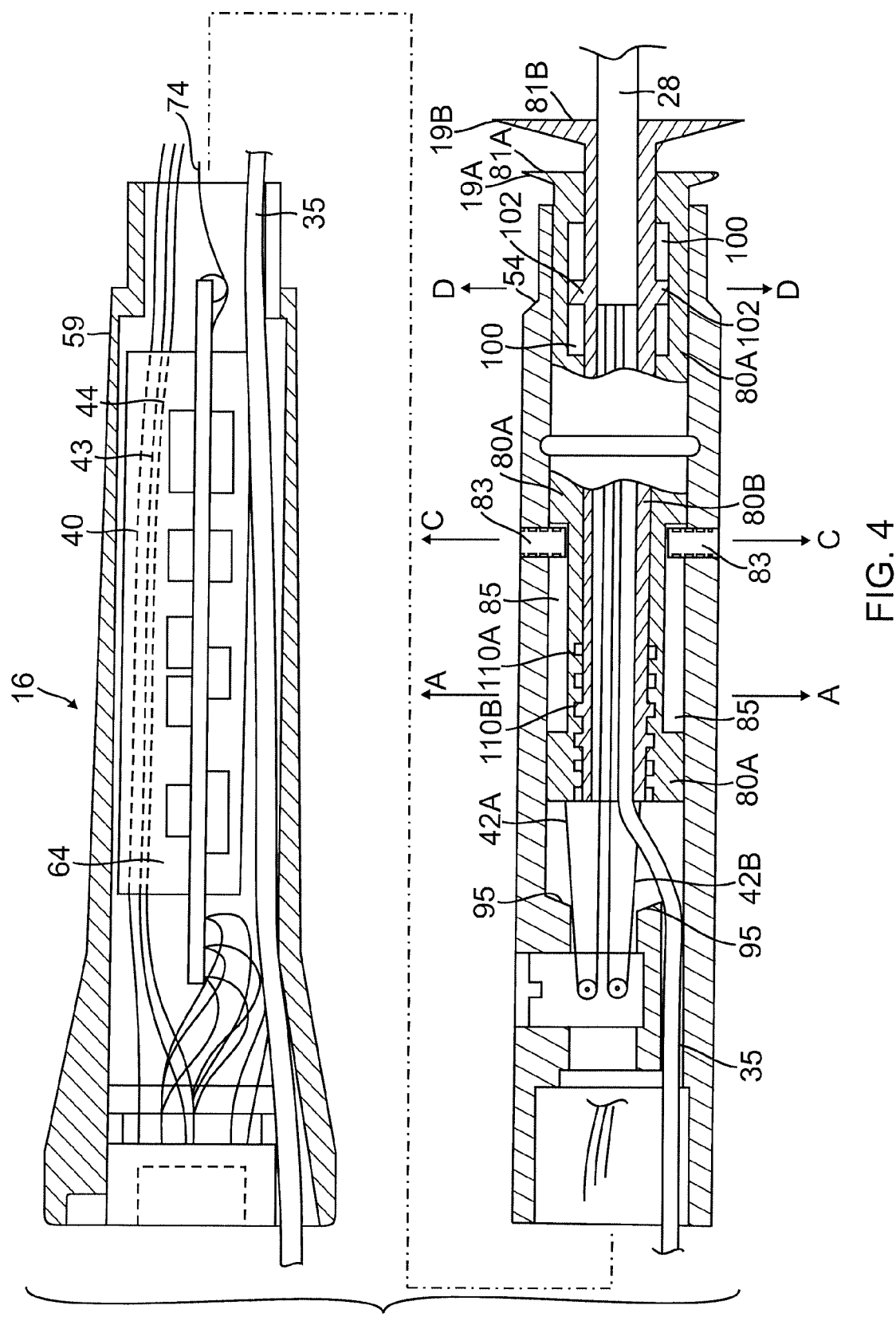
FIG. 4 is a side cross-sectional view of an embodiment of a control handle with thumb controls in an engaged configuration.

Longitudinal movement of the puller wires 42 relative to the catheter body 12, which results in deflection of selected sections of the intermediate section 14 is accomplished by suitable manipulation of the control handle 16. As shown in FIG. 4, the distal end of the control handle 16 comprises a piston 54 with a plurality of nested or stacked thumb controls 19 for manipulating the puller wires 42, where the plurality of thumb controls matches the plurality of puller wires. In the illustrated embodiment, the control handle has a first, outer and proximal thumb control 19A and a second, inner and distal thumb control 19B, with the distal thumb control 19B being concentrically nested in the proximal thumb control 19A. Each thumb control has an elongated proximal portion, for example a stem 80, and a wider distal portion, for example a conical or flared actuator 81. The thumb controls extend coaxially along a longitudinal axis of the piston, where the stem 80A of the proximal thumb control 19A is in a surrounding circumferential relationship with the stem 80B of the distal thumb control 19B. Each actuator 81 provides a user interface surface by which a user can move each thumb control longitudinally relative to the piston 54 and/or to each other by pushing or pulling on the neck with the user's thumb.

To prevent the proximal thumb control from sliding distally out of and separating from the piston, stops 83 extend inwardly from an outer wall of the piston 54 at a predetermined location. The stops are received in diametrically opposing slots 85 that extend longitudinally along an outer surface of the stem 80A. The slots 85 having a width (transverse to the longitudinal axis of the control handle) that closely matches that of the stops 83 also minimize rotational movement of the stem 80A about its longitudinal axis relative to the piston 54. Accordingly, the proximal thumb control 19A is allowed longitudinal movement only relative to the piston 54 of a maximum distance that is determined by and generally equal to the distance between the stop 83 and an inner surface abutment 95. Anchored to a proximal end of the stem 80A is a proximal end of the puller wire which is wrapped around a pulley 87A positioned proximal of the inner surface abutment 95. Thus, as the thumb control 19A is moved distally relative to the piston 54 by the user, the puller wire 42A anchored to the stem 80A is drawn distally to accomplish deflection along that puller wire distal of the compression coil 56A surrounding it.

To prevent the distal thumb control 19B from sliding distally out of and separating from the proximal thumb control 19A, the stem 80A of the proximal thumb control 19A is formed with diametrically opposing slots 100 that extend longitudinally along its outer surface. The slots 100 have a width that is at least about twice the width of longitudinally elongated raised formations or guides 102 formed on an outer surface of the stem 80B of the distal thumb control 19B. The length of the slots 100 limits the maximum distance of longitudinal movement of the distal thumb control 19B relative to the proximal thumb control 19A. Accordingly, the distal thumb control 19B is allowed longitudinal movement along with a predetermined amount of rotational movement relative to the proximal thumb control 19A between two positions, the significance of the latter of which is explained further below. Anchored to a proximal end of the stem 80B is a proximal end of the puller wire 42B which is wrapped around a pulley 87B positioned proximal of the inner surface abutment 95. Thus, as the thumb control 19B is moved distally relative to the piston 54 by the user, the puller wire 42B anchored to the stem 80B is drawn distally to accomplish deflection along that puller wire distal of the compression coil 56B surrounding it.

Figure 4A:
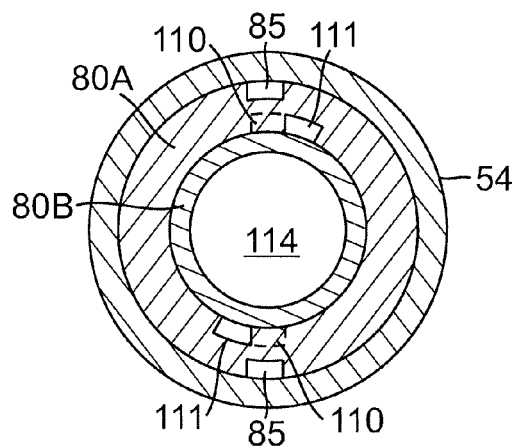
FIG. 4A is a longitudinal cross-sectional view of the control handle of FIG. 4, taken along line A-A, showing thumb controls in an engaged configuration.
Figure 4B:
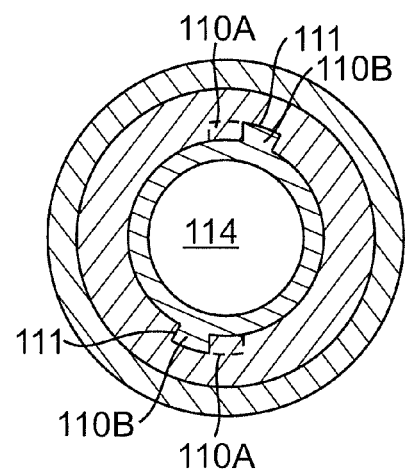
FIG. 4B illustrates the thumb controls of FIG. 4A in a disengaged configuration.
Figure 4C:
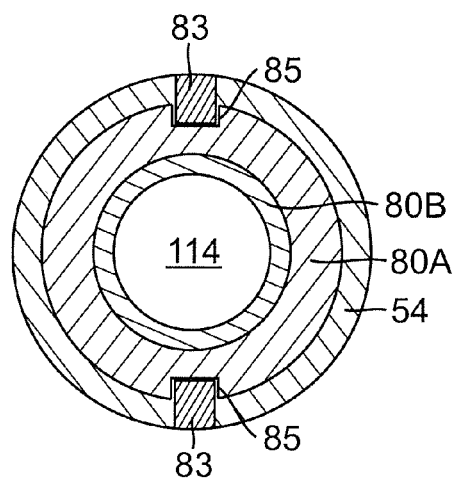
FIG. 4C is a longitudinal cross-sectional view of the control handle of FIG. 4, taken along line C-C.
Figure 4D:
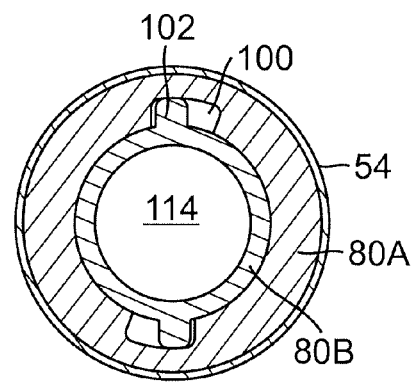
FIG. 4D is a longitudinal cross-sectional view of the control handle of FIG. 4, taken along line D-D.

To allow operation of the thumb controls between independent and selectively engaged longitudinal movements, releasably locking members, e.g., longitudinal rows of teeth 110A, 110B, are provided at interfacing surfaces of the respective stems. In the disclosed embodiment, inner surface of the stem 80A has a greater number of teeth and outer surface of the stem 80B has a lesser number of teeth and a longitudinal channel 111 is formed extending immediately adjacent and parallel to the row of the teeth 110A on the inner surface of the stem 80A of the proximal thumb control 19A. The channel has a width that is at least the width of the teeth so that the teeth of the stem 80B of the distal proximal thumb control 19B can be rotated out of engagement (for example, out of longitudinal alignment) with the teeth of the stem 80A of the proximal thumb control 19A so that the thumb controls can be longitudinally moved and adjusted independently of each other. In the illustrated embodiment, rotation of the inner thumb control in a clockwise direction disengages the respective teeth of the inner and outer thumb controls (FIG. 4B) and rotation in a counterclockwise direction engages the thumb controls so they can be moved as a single unit (FIG. 4A). In the latter regard, engagement of the teeth in different selective configurations advantageously provides different deflections or deflection combinations of the deflectable intermediate section.

In accordance with a feature of the invention, by rotating the thumb control(s) to disengage them from each other, each puller wire can be independently controlled by manipulation of each thumb control (FIG. 5) from a neutral, undeflected configuration (FIG. 7A). As such, precise control over the curve profiles of intermediate deflectable section 14 of the catheter. FIG. 7B illustrates independent deflection of the distal portion 14B of the intermediate section by means of independent distal longitudinal movement of the thumb control 19B that operates the longer puller wire. FIG. 7C illustrates independent deflection of the proximal portion 14A of the intermediate section by means of independent distal longitudinal movement of the thumb control 19A that operates the shorter puller wire. By rotating the thumb controls to engage each other, each puller wire can be simultaneously deflected by manipulation of any thumb control (FIG. 4). As such, the intermediate deflectable section is able to adopt a more uniform curve profile comparable to conventional catheters (FIG. 7D). By deflecting one puller as illustrated in FIG. 5 and then rotating the thumb control(s) to engage them, all puller wires can be simultaneously deflected by manipulation of any one thumb control with the pre-tensioned thumb control (FIG. 6). As such, simultaneous deflection of independent curve profiles is accomplished. FIG. 7E illustrates a pre-deflection of the distal portion (broken lines) followed by deflection of both distal and proximal portions accomplished through coupled thumb controls (solid lines). FIG. 7F illustrates a pre-deflection of the proximal portion (broken lines) followed by deflection of both distal and proximal portions accomplished through coupled thumb controls (solid lines). These and other combined deflections can be achieved by selective distal anchoring positions of the puller wires, selective engagement and operation of the thumb controls. In that regard, it is understood that the catheter of the disclosed embodiment can be pre-deflected by selective engagement of the thumb controls in terms of the thumb controls longitudinal position relative to each other when the inner thumb control is rotated counterclockwise to lock with the outer thumb control. The pre-deflection can then be further increased or tightened by actuation of the coupled thumb control. It is understood however that operation of the thumb controls can be in any order as desired or appropriate, that is, deflection of the catheter as a whole can occur before or after deflection of various sections and/or pre-deflection of various sections.

Visual and/or tactile indicia or markers can be provided on the actuators 81 of the thumb controls 19 to indicate alignment and/or nonalignment and hence engagement or disengagement of the releasable locking members between the thumb controls. The stem 80B of the inner thumb control 19B is hollow with a passage 114 to allow components such as the puller wires, lead wires, irrigation tubing, thermocouple wires and sensor cable to pass from the catheter body toward the proximal end of the control handle. These components pass into the control handle by means of a shrink sleeve 28 at the distal end of the inner thumb control 19B.

The embodiment of the control handle of FIG. 4 includes a proximal piston 59. The irrigation tubing 35, the lead wires 40 and the electromagnetic sensor cable 74, thermocouple wires extend into the proximal piston. The electromagnetic sensor cable 74 connects to the circuit board 64. Wires 73 connect the circuit board 64 to a computer and imaging monitor (not shown). Guide tubes are provided in the control handle to allow longitudinal movement of these components as needed.

The illustrated embodiment of FIG. 2 provides both puller wires 42A and 42B extending through a single lumen. Thus, deflection of the proximal portion 14A and the distal portion 14B are intended to be toward the same general direction and in a single plane. Alternatively, the puller wires can extend through adjacent lumens, such as illustrated in FIG. 2B, for deflection of the proximal portion 14A and the distal portion 14B in offset planes, where the degree of offset depends on the offset degree of the respective lumens. In the illustrated embodiment of FIG. 2B, the offset degree is about 90 degrees.

The present invention is not limited to two thumb controls and two puller wires. It is understood that any number of thumb controls and a common number of puller wires falls within the scope of the present invention as the control handle can readily accommodate a greater number of nested thumb controls as appropriate or desired.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body;
    a deflectable intermediate section having at least a first portion and a second portion;
    a control handle proximal the elongated body, the control handle including at least first and second thumb controls, the first thumb control connected to a first puller wire extending through the first portion, and the second thumb control connected to a second puller wire extending through the second portion,
    wherein the first and second thumb controls include releasable engagement members movable between a disengagement configuration and an engagement configuration, wherein the disengagement configuration allows independent longitudinal movement of the first and second thumb controls relative to each other and the engagement configuration couples the first and second thumb controls to each other for longitudinal movement of the first and second thumb controls relative to the control handle.

2. A catheter of claim 1, wherein the first and second thumb controls are in a nested configuration such that one of the first or second thumb controls is nested in the other of the first or second thumb controls.

3. A catheter of claim 1, wherein each of the first and second thumb controls has a stem portion and a neck portion, wherein the stem portion of one of the first or second thumb controls is in an outer circumferential relationship with the stem portion of the other of the first or second thumb control.

4. A catheter of claim 1, wherein the releasable engagement members include teeth on interfacing surfaces of the first and second thumb controls.

5. A catheter of claim 3, wherein the releasable engagement members comprise a first set of releasable engagement members on an inner surface of the stem portion of the first thumb control and a second set of releasable engagement members on an outer surface of the stem portion of the second thumb control.

6. A catheter of claim 5, wherein the first set and second set of releasable engagement members are engaged via rotation of one of the first or second thumb controls relative to the other of the first or second thumb controls.

7. A catheter of claim 1, wherein the control handle includes a piston and at least one stop, wherein the stop is configured to guide longitudinal movement of the first thumb control relative to the piston and to minimize rotational movement of the first thumb control relative to the piston.

8. A catheter of claim 1, wherein the first and second thumb controls are configured for longitudinal movement relative to each other.

9. A catheter of claim 1, wherein the first and second thumb controls are configured for rotational movement relative to each other, whereby rotation of one of the first or second thumb controls in a first direction enters the first and second thumb controls into the disengagement configuration, and rotation of one of the first or second thumb controls in a second direction enters the first and second thumb controls into the engagement configuration.

10. A catheter of claim 1, wherein one of the first or second puller wires is a longer puller wire and the other of the first or second puller wires is a shorter puller wire.

11. A catheter of claim 10, wherein the longer puller wire has a first distal anchor location and the shorter puller wire has a second distal anchor location, and one of the first or second distal anchor locations is more distal from the control handle than the other of the first or second distal anchor locations.

12. A catheter of claim 11, further comprising:
    a shorter compression coil in surrounding relationship with the shorter puller wire, the shorter compression coil having a distal end at or near a proximal end of the deflectable intermediate section;
    a longer compression coil in surrounding relationship with the longer puller wire, the longer compression coil having a distal end at or near a distal end of the shorter puller wire.

13. A catheter comprising:
    an elongated catheter body;
    a deflectable intermediate section having at least a distal deflectable portion and a proximal deflectable portion;
    a control handle proximal the elongated catheter body, the control handle including at least an outer thumb control and an inner thumb control;
    a longer puller wire having a proximal end anchored in the inner thumb control and a distal end anchored at or near a distal end of the distal deflectable portion;
    a shorter puller wire having a proximal end anchored in the outer thumb control and a distal end anchored at or near a distal end of the proximal deflectable portion;
    a shorter compression coil in surrounding relationship with the shorter puller wire, the shorter compression coil having a distal end at or near a proximal end of the deflectable intermediate section;
    a longer compression coil in surrounding relationship with the longer puller wire, the longer compression coil having a distal end at or near the distal end of the shorter puller wire,
    wherein the inner and outer thumb controls include releasable engagement members movable between a disengagement configuration and an engagement configuration, wherein the disengagement configuration allows independent longitudinal movement of the inner and outer thumb controls relative to each other and the engagement configuration couples the inner and outer thumb controls to each other for longitudinal movement of the inner and outer thumb controls relative to the control handle.

14. A catheter of claim 13, wherein each of the inner and outer thumb controls has a stem portion and a neck portion, wherein the stem portion of one of the inner or outer thumb controls is in an outer circumferential relationship with the stem portion of the other of the inner or outer thumb controls.

15. A catheter of claim 13, wherein the releasable engagement members include teeth on interfacing surfaces of the inner and outer thumb controls.

16. A catheter of claim 14, wherein the releasable engagement members comprise a first set of releasable engagement members on an inner surface of the stem portion of the outer thumb control and a second set of releasable engagement members on an outer surface of the stem portion of the inner thumb control.

17. A catheter of claim 16, wherein the first set and second set of releasable engagement members are engaged via rotation of one of the inner or outer thumb controls relative to the other of the inner or outer thumb controls.

18. A catheter of claim 13, wherein the control handle includes a piston and at least one stop, wherein the at least one stop is configured to guide longitudinal movement of the outer thumb control relative to the piston and to minimize rotational movement of the outer thumb control relative to the piston.

19. A catheter of claim 13, further comprising at least one guide on an interfacing surface between the inner and the outer thumb control to guide longitudinal movement of the thumb controls relative to each other.

20. A catheter of claim 19, further comprising at least one slot for receiving the at least one guide, the at least one slot being on another interfacing surface between the inner and the outer thumb control to provide rotational movement of the thumb controls relative to each other.

* * * * *